(12) United States Patent
Marczyk et al.

(10) Patent No.: US 11,103,246 B2
(45) Date of Patent: Aug. 31, 2021

(54) MULTI-FIRE STAPLER WITH ELECTRONIC COUNTER, LOCKOUT, AND VISUAL INDICATOR

(71) Applicant: Covidien LP, Mansfield, MA (US)

(72) Inventors: Stanislaw Marczyk, Stratford, CT (US); Stanislaw Kostrzewski, Newtown, CT (US); Philip Irka, Madison, CT (US); David Racenet, Killingworth, CT (US)

(73) Assignee: Covidien LP, Mansfield, MA (US)

( * ) Notice: Subject to any disclaimer, the term of this patent is extended or adjusted under 35 U.S.C. 154(b) by 192 days.

(21) Appl. No.: 16/260,385

(22) Filed: Jan. 29, 2019

(65) Prior Publication Data

US 2019/0150925 A1 May 23, 2019

Related U.S. Application Data

(60) Division of application No. 14/973,018, filed on Dec. 17, 2015, now Pat. No. 10,194,907, which is a
(Continued)

(51) Int. Cl.
*A61B 17/072* (2006.01)
*A61B 90/98* (2016.01)
(Continued)

(52) U.S. Cl.
CPC ........ *A61B 17/07207* (2013.01); *A61B 90/98* (2016.02); *A61B 2017/00017* (2013.01);
(Continued)

(58) Field of Classification Search
CPC ............. A61B 17/07207; A61B 90/98; A61B 2090/0803; A61B 2090/0807;
(Continued)

(56) References Cited

U.S. PATENT DOCUMENTS

| 3,650,453 A | 3/1972 | Smith, Jr. |
| 3,717,294 A | 2/1973 | Green |

(Continued)

FOREIGN PATENT DOCUMENTS

| CN | 102860851 A | 1/2013 |
| EP | 0156774 A2 | 10/1985 |

(Continued)

OTHER PUBLICATIONS

Australian Office Action dated Sep. 21, 2020, issued in AU Appln. No. 201626237, 5 pages.

(Continued)

*Primary Examiner* — Michelle Lopez
(74) *Attorney, Agent, or Firm* — Carter, DeLuca & Farrell LLP

(57) ABSTRACT

A surgical system includes a handle having a controller and a motor, an adapter releasably coupled to the handle, and a loading unit releasably coupled to the adapter. The motor is coupled to a drive shaft of the handle. The adapter including an adapter identification device in communication with the controller, configured to store adapter data, and to communicate the adapter data to the controller. The loading unit configured to affect tissue in response to a force transmitted by the adapter from the drive shaft. The loading unit including a loading unit identification device in communication with the controller, configured to store loading unit data, and to communicate the loading unit data to the controller. The controller is configured to adjust output of a motor based on at least one of the adapter data or the loading unit data.

9 Claims, 3 Drawing Sheets

Related U.S. Application Data continuation-in-part of application No. 13/899,882, filed on May 22, 2013, now Pat. No. 9,554,796.

(60) Provisional application No. 61/672,882, filed on Jul. 18, 2012.

(51) Int. Cl.
*A61B 17/00* (2006.01)
*A61B 90/00* (2016.01)

(52) U.S. Cl.
CPC ............ *A61B 2017/00022* (2013.01); *A61B 2017/0046* (2013.01); *A61B 2017/00075* (2013.01); *A61B 2017/00084* (2013.01); *A61B 2017/00115* (2013.01); *A61B 2017/00199* (2013.01); *A61B 2017/00398* (2013.01); *A61B 2017/00473* (2013.01); *A61B 2017/07235* (2013.01); *A61B 2017/07242* (2013.01); *A61B 2017/07271* (2013.01); *A61B 2090/0803* (2016.02); *A61B 2090/0807* (2016.02); *A61B 2090/0811* (2016.02); *A61B 2090/0814* (2016.02)

(58) Field of Classification Search
CPC .... A61B 2090/0811; A61B 2090/0814; A61B 2017/00017; A61B 2017/0022; A61B 2017/00115; A61B 2017/00199; A61B 2017/00398; A61B 2017/07235; A61B 2017/07242; A61B 2017/07271
USPC ........................................................ 227/175.1
See application file for complete search history.

(56) References Cited

U.S. PATENT DOCUMENTS

| | | |
|---|---|---|
| 3,837,555 A | 9/1974 | Green |
| 4,612,933 A | 9/1986 | Brinkerhoff et al. |
| 4,892,244 A | 1/1990 | Fox et al. |
| 4,951,860 A | 8/1990 | Peters et al. |
| 4,955,959 A | 9/1990 | Tompkins et al. |
| 5,246,156 A | 9/1993 | Rothfuss et al. |
| 5,313,935 A | 5/1994 | Kortenbach et al. |
| 5,413,267 A | 5/1995 | Solyntjes et al. |
| 5,415,335 A | 5/1995 | Knodell, Jr. |
| 5,472,132 A | 12/1995 | Savage et al. |
| 5,487,499 A | 1/1996 | Sorrentino et al. |
| 5,709,334 A | 1/1998 | Sorrentino et al. |
| 5,752,644 A | 5/1998 | Bolanos et al. |
| 5,865,361 A | 2/1999 | Milliman et al. |
| 5,893,506 A | 4/1999 | Powell |
| 5,991,355 A | 11/1999 | Dahlke |
| 6,079,606 A | 6/2000 | Milliman et al. |
| 6,109,500 A | 8/2000 | Alli et al. |
| 6,155,473 A | 12/2000 | Tompkins et al. |
| 7,934,631 B2 | 5/2011 | Balbierz et al. |
| 7,954,683 B1 | 6/2011 | Knodel et al. |
| 7,963,432 B2 | 6/2011 | Knodel et al. |
| 8,070,033 B2 | 12/2011 | Milliman et al. |
| 8,499,993 B2 | 8/2013 | Shelton, IV et al. |
| 9,016,539 B2 | 4/2015 | Kostrzewski et al. |
| 9,055,943 B2 | 6/2015 | Zemlok et al. |
| 2005/0222616 A1 | 10/2005 | Rethy et al. |
| 2007/0034667 A1 | 2/2007 | Holsten et al. |
| 2011/0121049 A1 | 5/2011 | Malinouskas et al. |
| 2011/0125138 A1 | 5/2011 | Malinouskas et al. |
| 2011/0139851 A1* | 6/2011 | McCuen ................ A61B 34/76 227/175.1 |
| 2011/0192881 A1 | 8/2011 | Balbierz et al. |
| 2011/0295269 A1 | 12/2011 | Swensgard et al. |
| 2012/0089131 A1 | 4/2012 | Zemlok et al. |
| 2014/0021239 A1 | 1/2014 | Kostrzewski |
| 2014/0103092 A1 | 4/2014 | Kostrzewski et al. |
| 2015/0088115 A1 | 3/2015 | Smith |
| 2015/0303996 A1 | 10/2015 | Calderoni |
| 2015/0324317 A1 | 11/2015 | Collins et al. |

FOREIGN PATENT DOCUMENTS

| | | |
|---|---|---|
| EP | 2090241 A1 | 8/2009 |
| EP | 2130498 A1 | 12/2009 |
| EP | 2332471 A1 | 6/2011 |
| EP | 2540231 A2 | 1/2013 |
| EP | 2772206 A2 | 9/2014 |
| EP | 2942016 A1 | 11/2015 |
| EP | 3070627 A1 | 9/2016 |
| JP | 2009022742 A | 2/2009 |
| JP | 2009189841 A | 8/2009 |
| JP | 2011104379 A | 6/2011 |
| JP | 2015213752 A | 12/2015 |
| WO | 2010/054404 A1 | 5/2010 |

OTHER PUBLICATIONS

Chinese Office Action dated Apr. 19, 2017 in corresponding Chinese Patent Application No. 201310303617.6 together with English translation, 17 pages.
European Search Report dated May 10, 2017 in corresponding European Patent Application No. 16204707, 8 pages.
European Search Report EP 13 17 6778 dated Oct. 28, 2013.
European Office Action dated Feb. 16, 2017 in corresponding European Patent Application No. 15197144.7, 4 pages
Japanese Office Action (with English translation), dated Oct. 23, 2020, corresponding to counterpart Japanese Application No. 2016-237446; 13 total pages.
English translation of Japanese Office Action dated Feb. 25, 2021, corresponding to Japanese Application No. 2016-237446; 6 pages.

\* cited by examiner

MULTI-FIRE STAPLER WITH ELECTRONIC COUNTER, LOCKOUT, AND VISUAL INDICATOR

CROSS-REFERENCE TO RELATED APPLICATIONS

This application is a Divisional of U.S. patent application Ser. No. 14/973,018, filed on Dec. 17, 2015, which is a Continuation-in-Part and claims the benefit of, and priority to, U.S. patent application Ser. No. 13/899,882, filed May 22, 2013, now U.S. Pat. No. 9,554,796, which claims the benefit of, and priority to, U.S. Provisional Patent Application Ser. No. 61/672,882, filed Jul. 18, 2012, the entire content of each of which is hereby incorporated by reference.

BACKGROUND

1. Technical Field

The present disclosure relates to surgical stapling systems and, more particularly, to multi-fire surgical stapling systems including an electronic counter, a lockout, and a visual indicator mechanism for indicating the condition or state of the system.

2. Discussion of Related Art

Surgical staplers that first grasp or clamp tissue between opposing structures and then join the tissue with surgical fasteners are well known in the art. In some devices, a knife cuts the tissue that has been joined by the fasteners. The fasteners are typically in the form of surgical staples but other devices, such as two-part polymeric fasteners have also been utilized.

Surgical staplers may be linear surgical staplers that include two jaw structures which capture or clamp tissue therebetween. Typically, one of the jaw structures carries a staple cartridge which houses a plurality of staples arranged in at least two lateral rows, while the other member has an anvil that defines a surface for forming the staple legs as the staples are driven from the staple cartridge. Generally, the stapling operation is effected by a cam bar, a drive sled, or other similar mechanism, that travels longitudinally through the staple cartridge to sequentially eject the staples from the staple cartridge. A knife may also travel between the staple rows to longitudinally cut the stapled tissue between the rows of staples.

Surgical staplers may also be circular surgical staplers that include two structures which capture or clamp tissue therebetween. Typically, one of the structures carries a staple cartridge which houses a plurality of staples arranged in at least two circular rows, while the other member has an anvil that defines a surface for forming the staple legs as the staples are driven from the staple cartridge. Generally, the stapling operation is effected by a longitudinally driven drive bar, or other similar mechanism, that travels through the staple cartridge to simultaneously eject the staples from the staple cartridge. A knife may also travel between the staple rows to circularly cut the stapled tissue within the inner row of staples.

In endoscopic or laparoscopic procedures, surgery is performed through a small incision or through a narrow cannula inserted through small entrance openings in the skin. In order to address the specific needs of endoscopic and/or laparoscopic surgical procedures, endoscopic surgical stapling devices have also been developed.

It would be beneficial, particularly with respect to laparoscopic and/or endoscopic surgical procedures, to provide a surgical stapler that can provide a predetermined number of firings without requiring removal of the stapler from the surgical site and that also includes a lockout mechanism for preventing "empty firing," e.g., firing beyond the expiration of a pre-determined number of firings, and/or firing after a partial firing has occurred. In addition, it would be beneficial to provide a visual indicator that indicates the condition or state of the stapler, e.g., the number of times the stapler has been fired, the number of firings remaining, or whether the stapler is locked out. Further, it would be beneficial to gather data about the firings of the stapler for use by the medical facility or the manufacturer of the stapler.

SUMMARY

In an aspect of the present disclosure, a surgical stapling system includes a handle, an adapter, and a loading unit. The handle includes a controller and a motor that is coupled to a drive shaft. The adapter is releasably coupled to the handle and includes an adapter identification device that is in communication with the controller. The adapter identification device is configured to store adapter data and to communicate the adapter data to the controller. The loading unit is releasably coupled to the adapter. The loading unit is configured to affect tissue in response to a force transmitted by the adapter from the drive shaft. The loading unit includes a loading unit identification device in communication with the controller. The loading unit identification device is configured to store loading unit data and is configured to communicate the loading unit data to the controller. The controller is configured to adjust output of the motor based on at least one of the adapter data or the loading unit data.

In aspects, the surgical system includes a force gauge that is disposed within the adapter configured to measure a force exerted on the loading unit. The force gauge may be in communication with the adapter identification device and configured to transmit the measured force to the adapter identification device.

In some aspects, the surgical system includes a console in communication with the controller and a monitor in communication with the console. The monitor is configured to display at least one of the adapter data or the loading unit data that is transmitted by the controller.

In certain aspects, the output of the motor is controlled based on at least one of the measured force exerted on the loading unit, the adapter data, the loading unit data, or a lockout condition of the loading unit. The loading unit data may include a type of loading unit, a production lot number of the loading unit, a serial number of the loading unit, a calibration constant of the loading unit, a length of a stapling line of the loading unit, a staple size of the loading unit, a number of completed firings of the loading unit, a maximum number of firings of the loading unit, or a manufacturer of the loading unit. The loading unit identification device may update the loading unit data in response to the loading unit affecting tissue. The loading unit identification device may update a number of completed firings, a peak force during firing, a total amount of force applied to the loading unit during firing, a total amount of work done by the loading unit, a peak retraction force, an articulation angle during firing, a number of pauses during firing, or a thickness of tissue during each firing.

In particular aspects, the controller is configured to calculate the highest peak force applied to the loading unit and to verify that the highest peak force is within a predefined peak force range. The controller may be configured to calculate the total work done during actuation of the loading unit and to verify that the total work done is below a predefined total work limit. The controller may be configured to prevent actuation of the loading unit in response to a number of completed actuations of a loading unit being equal to or greater than a maximum number of available actuations of the loading unit, a actuation of the loading unit being incomplete, a peak force of a actuation being outside of a predefined peak force range, or a total amount of work done during completed actuations being equal to or greater than a predefined total work limit. The controller may be configured to provide indicia to a user of a number of available actuations of the loading unit.

In aspects, the loading unit includes a replaceable multi-fire fastener cartridge in communication with the loading unit identification device to update the loading unit data.

In another aspect of the present disclosure, a method of actuating a surgical system includes coupling a loading unit to a handle via an adapter, reading loading unit data from a loading unit identification device of the loading unit with a controller of the handle, enabling actuation of the loading unit in response to the loading unit data meeting a predefined condition, recording event data during actuation of the loading unit, and updating the loading unit data with the event data.

In aspects, the method may include displaying a portion of the loading unit data on a display disposed on the handle. The method may also include displaying, on the display of the handle, a recommended multi-fire fastener cartridge for the loading unit in response to the event data.

In some aspects, the method includes the controller preventing the loading unit from firing when the loading unit does not meet the predefined conditions. The method may include recommending a second loading unit from the loading unit data before enabling actuation of the loading unit.

In certain aspects, the method includes detaching the loading unit from the adapter, attaching a second loading unit to the adapter, reading second loading unit data from a second loading unit identification device with the controller, enabling actuation of the second loading unit in response to the second loading unit data meeting the at least one predefined condition, recording event data during actuation of the second loading unit, and updating the second loading unit data with the event data.

In particular aspects, the method includes recommending a second multi-fire fastener cartridge for the loading unit from the loading unit data before enabling actuation of the loading unit. The method may include removing a first multi-fire fastener cartridge from the loading unit, attaching a second multi-fire fastener cartridge to the loading unit, and reading multi-fire fastener cartridge data from a multi-fire fastener cartridge identification device of the second multi-fire fastener cartridge with the loading unit identification device. The method may include updating the loading unit data with the loading identification device after reading the multi-fire fastener cartridge data of the second multi-fire fastener cartridge. The loading unit data including a type of fastener within the second multi-fire fastener cartridge, a production lot number of the second multi-fire fastener cartridge, a serial number of the second multi-fire fastener cartridge, a fastener size of fasters within the second multi-fire fastener cartridge, a completed number of firings of the second multi-fire fastener cartridge, a maximum number of firings the second multi-fire fastener cartridge, or a manufacturer of the second multi-fire fastener cartridge.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
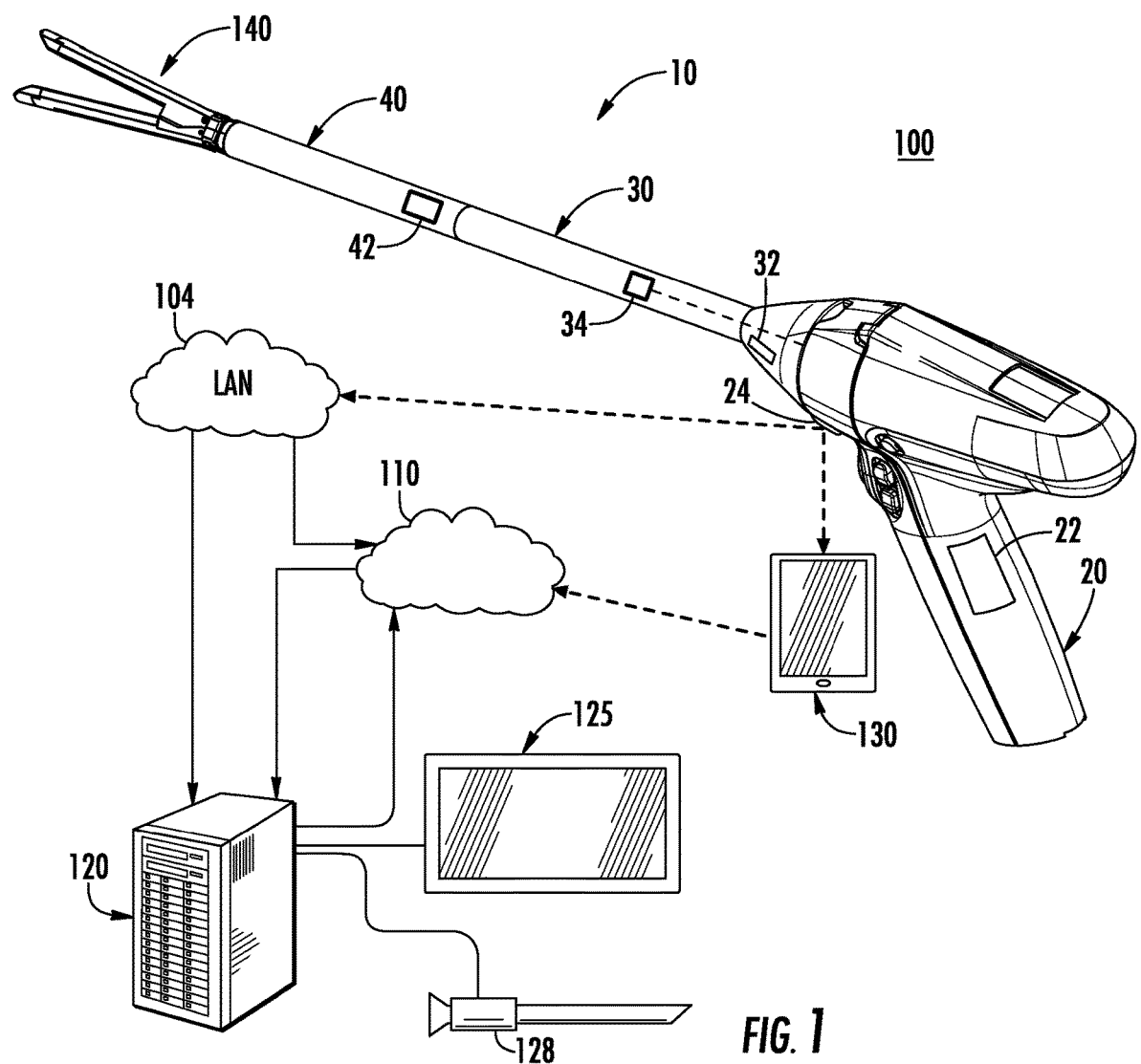
FIG. 1 is a schematic drawing of an exemplary embodiment of a surgical system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Referring now to FIG. 1, a surgical system 100 is provided in accordance with the present disclosure and includes a surgical instrument 10 that is in communication with a console 120 or a portable device 130 through a local area network 104 or a cloud network 110 via a wired or wireless connection. In embodiments, console 120 and the portable device 130 may be any suitable computing device.

An exemplary embodiment of a surgical instrument 10 is disclosed in U.S. Pat. No. 9,055,943, the contents of which are hereby incorporated by reference in their entirety.

Figure 2:
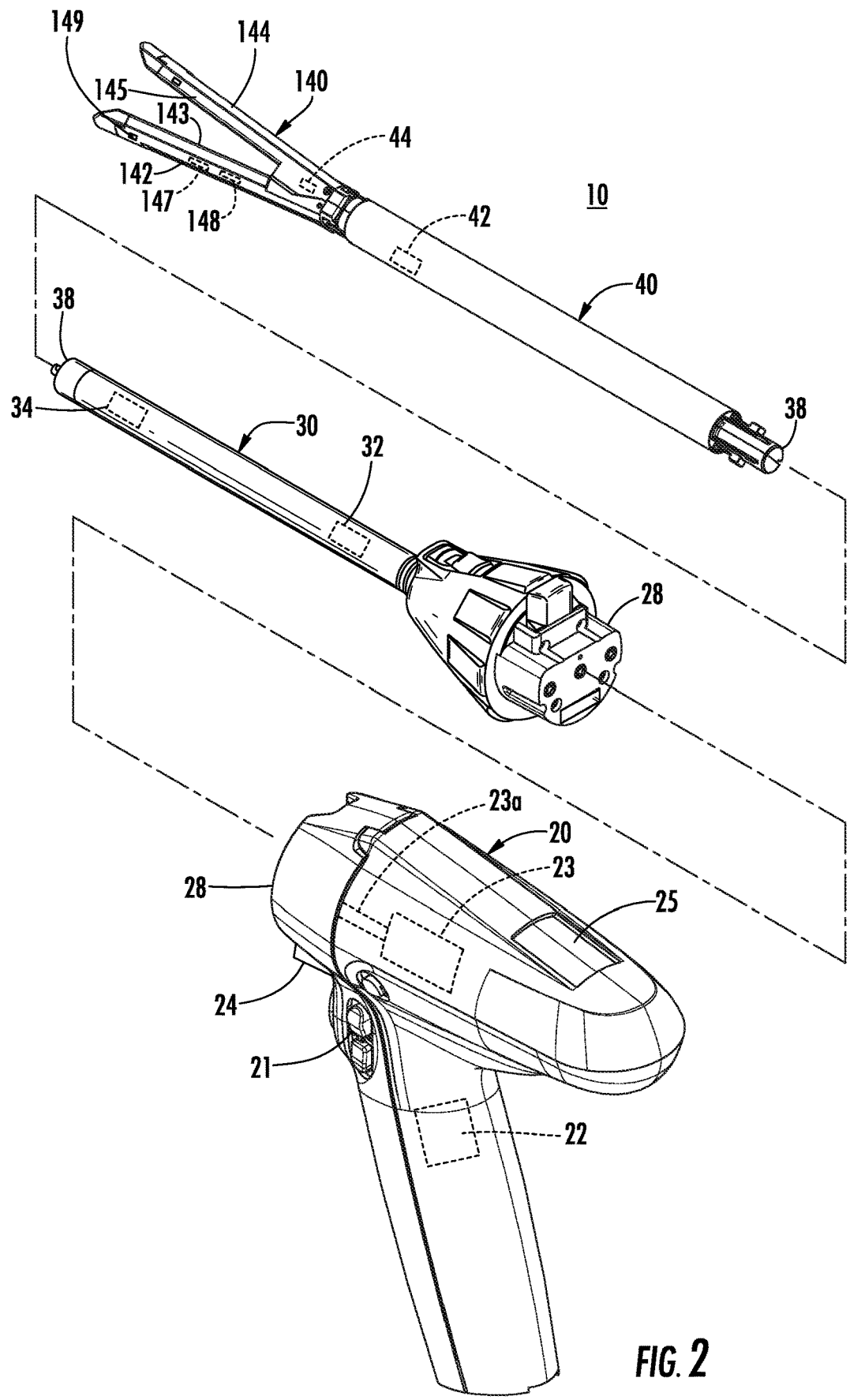
FIG. 2 is perspective view of a surgical instrument of the surgical system of FIG. 1.

With additional reference to FIG. 2, the surgical instrument 10 includes a handle 20, an adapter 30, and a loading unit 40. The adapter 30 releasably couples to the handle 20 and the loading unit 40 releasably couples to the adapter 30 such that the adapter 30 transmits a force from a drive shaft 23*a* to the loading unit 40. The adapter 30 or the loading unit 40 may include a force gauge (not explicitly shown) disposed therein to measure a force exerted on the loading unit 40. The loading unit 40 includes an end effector 140 having a first jaw 142 and a second jaw 144. The loading unit 40 may be a an in-situ loaded or multi-firing loading unit (MFLU) that allows a clinician to fire a plurality of fasteners multiple times without requiring the loading unit 40 to be removed from a surgical site to reload the loading unit 40. An exemplary embodiment of such a MFLU is disclosed in U.S. Pat. No. 9,016,539, U.S. Patent Publication Nos. 2014/0021239, 2014/0103092, the contents of each of the above disclosures are incorporated by reference in their entirety.

The first and second jaws 142, 144 are configured to clamp tissue therebetween, fire fasteners through the clamped tissue, and sever the clamped tissue. The first jaw 142 may be configured to fire at least one fastener a plurality of times, or may be configured to include a replaceable multi-fire fastener cartridge 143 including a plurality of fasteners (e.g., staples, clips, etc.) that may be fired more that one time prior to being replaced. The multi-fire fastener cartridge 143 may be releasably coupled to the first jaw 142 or may be integrally formed with the first jaw 142. The second jaw 144 may include an anvil 145 that deforms or otherwise secures the fasteners about tissue as the fasteners are ejected from the multi-fire fastener cartridge 143. The multi-fire fastener cartridge 143 may also include a cartridge identification device 147 that stores and transmits cartridge data as detailed below.

With continued reference to FIG. 2, the handle 20 includes a motor 23 that is coupled to the drive shaft 23*a* to affect rotation of the drive shaft 23*a*. The handle 20 includes a control interface 21 to selectively activate the motor 23. The control interface 21 may include buttons, switches, levers, sliders, touch screen, and any other suitable input mechanisms or user interfaces, which can be engaged by a clinician to activate the motor 23.

The control interface 21 of the handle 20 is in communication with a controller 22 of handle 20 to selectively activate the motor 23 to affect rotation of the drive shafts 23*a*. The controller 22 is disposed within the handle 20 and is configured to receive input from the control interface 21 and adapter data from the adapter 30 or loading unit data from the loading unit 40. The controller 22 analyzes the input from the control interface 21 and the data received from the adapter 30 and/or loading unit 40 to selectively activate the motor 23 as detailed below. The handle 20 may also include a display 25 that is viewable by a clinician during use of the handle 20. The display 25 is configured to display portions of the adapter or loading unit data before, during, or after firing of the instrument 10.

The controller 22 is configured to "lock out" or prevent actuation, e.g., firing, of the loading unit 40 if a value of the data received from the adapter 30 or the loading unit 40 is outside a predefined range or does not meet a predefined condition as detailed below. The controller 22 may display an error, including the value or the predefined condition that was not met, on the display 25. Additionally or alternatively, the controller 22 may display a recommendation for a new or different loading unit in response to a value of the data received from the adapter 30 or the loading unit 40 as detailed below. In addition, the controller 22 may transmit the error or the recommendation to another component (e.g., console 120 and/or portable device 130) of the surgical system 100 (FIG. 1) that may display the error or recommendation to a clinician.

The adapter 30 includes an adapter identification device 32 disposed therein and the loading unit 40 includes a loading unit identification device 42 disposed therein. The adapter identification device 32 is in communication with the controller 22, and the loading unit identification device 42 is in communication with the controller 22. It will be appreciated that the loading unit identification device 42 may be in communication with the adapter identification device 32, which relays or passes communication from the loading unit identification device 42 to the controller 22.

The handle 20 and the adapter 30 are configured to interconnect the adapter identification device 32 and the loading unit identification device 42 with the controller 22 via an electrical interface 28. The electrical interface 28 may be a direct electrical interface (i.e., include electrical contacts that engage one another to transmit energy and signals therebetween). Additionally or alternatively, the electrical interface 28 may be a non-contact electrical interface to wirelessly transmit energy and signals therebetween (e.g., inductively transfer). It is also contemplated that the adapter identification device 32 and the controller 22 may be in wireless communication with one another via a wireless connection separate from the electrical interface 28.

The electrical interface 28 transmits energy from the handle 20 to the adapter 30, and adapter data from the adapter identification device 32 and the loading unit identification device 42 to the controller 22. In particular, the loading unit identification device 42 is interconnected to the adapter 30 via an electrical interface 38 as described in further detail below. The adapter data of the adapter identification device 32 may include, but is not limited to, whether a loading unit is attached to the adapter 30, a production lot number of the adapter 30, a serial number of the adapter 30, one or more calibration constants of the adapter 30 (e.g., to associate the motor 23 with the loading unit 40, set maximum and minimum torque of the motor 23), a completed number of actuations of the adapter 30, maximum number of actuations of the adapter 30, a manufacturer of the adapter 30, and the like. In addition, the electrical interface 28 may transmit control signals from the controller 22 to the adapter identification device 32 and to the loading unit identification device 42.

The adapter 30 and the loading unit 40 also include the electrical interface 38 therebetween to transmit energy from the adapter 30 or the handle 20 to the loading unit 40 and to transmit loading unit data of the loading unit identification device 42 to the adapter identification device 32 or the controller handle 22. Similar to the electrical interface 28, the electrical interface 38 may be a direct or non-contact electrical interface. It is also contemplated that the loading unit identification device 42 may be in wireless communication with the controller 22 or with the adapter identification device 32. The loading unit data may include, but is not limited to, a type of the loading unit 40, a production lot number of the loading unit 40, a serial number of the loading unit 40, one or more calibration constants of the loading unit 40, a length of a stapling line of the loading unit 40, a fastener size of the loading unit 40, a completed number of firings of the loading unit 40, maximum number of firings of the loading unit 40, a production date of the loading unit 40, a use-by or expiration date of the loading unit 40, or a manufacturer of the loading unit 40. In addition, the electrical interface 38 may transmit control signals from the controller 22 or from the adapter identification device 32 to the loading unit identification device 42.

An exemplary non-contact electrical interface is disclosed in U.S. Patent Publication Nos. 2015/0088115 and 2015/0303996, the entire contents of each are hereby incorporated by reference in their entirety.

The adapter 30 may also include a plurality of sensors 34 (one shown) disposed thereabout to detect various conditions of the adapter 30 or of the environment (e.g., if the adapter 30 is connected to a loading unit, if the adapter 30 is connected to a handle, if the drive shafts 23 are rotating, the torque of the drive shafts 23, the strain of the drive shafts 23, the temperature within the adapter 30, a number of firings of the adapter 30, a peak force of the adapter 30 during firing, a total amount of force applied to the adapter 30, a peak retraction force of the adapter 30, a number of pauses of the adapter 30 during firing, etc.). The plurality of sensors 34 provides an input to the adapter identification device 32 in the form of data signals. The data signals of the plurality of sensors 34 may be stored within, or be used to update the adapter data stored within, the adapter identification device 32. The data signals of the plurality of sensors 34 may be analog or digital. The plurality of sensors 34 may include a force gauge to measure a force exerted on the loading unit 40 during firing.

The loading unit 40 may include a plurality of sensors 44 (one shown) disposed thereabout to detect various conditions of the loading unit 40 or of the environment (e.g., if the loading unit 40 is connected to an adapter, the number of firings available for the loading unit 40, the work done by the loading unit 40, the temperature within the adapter 40, properties of a multi-fire cartridge attached to the loading unit 40, a complete number of firing of the multi-fire cartridge, a completed number of firings of the loading unit 40, a maximum number of firings of the loading unit 40, a peak force during firing of the loading unit 40, a total amount of force applied to the loading unit 40, a peak retraction force of the loading unit 40, an articulation angle during firing of the loading unit 40, a number of pauses during firing of the loading unit 40, a thickness of tissue during each firing of the loading unit 40, a production date of the loading unit 40, a use-by or expiration date of the loading unit 40, etc.). The plurality of sensors 44 provides an input to the loading unit identification device 42 in the form of data signals. The data signals of the plurality of sensors 44 may be stored within, or be used to update the loading unit data stored within, the loading unit identification device 42. The data signals of the plurality of sensors 44 may be analog or digital. The plurality of sensors 44 may include a force gauge to measure a force exerted on the loading unit 40 during firing.

The multi-fire fastener cartridge 143 and the loading unit 40 may include an electrical interface 149 therebetween to transmit energy from the loading unit 40, the adapter 30, or the handle 20 to the fastener cartridge 143, and to transmit the cartridge data of the multi-fire fastener cartridge 143 to the loading unit identification device 42, the adapter identification device 32, or the controller 22. The cartridge data may include, but is not limited to, a type of the multi-fire fastener cartridge 143, a production lot number of the multi-fire fastener cartridge 143, a serial number of the multi-fire fastener cartridge 143, a calibration constant of the multi-fire fastener cartridge 143, a length of a stapling line of the multi-fire fastener cartridge 143, a fastener size of the multi-fire fastener cartridge 143, a completed firing indication of the multi-fire fastener cartridge 143, an indication of the firings remaining of the multi-fire fastener cartridge 143, an indication that all firings of the multi-fire fastener cartridge 143 have been used, a production date of the multi-fire fastener cartridge 143, a use-by or expiration date of the multi-fire fastener cartridge 143, or a manufacturer of the multi-fire fastener cartridge 143. In addition, the electrical interface 149 may transmit control signals from the controller 22, the adapter identification device 32, or the loading unit identification device 42 to the cartridge identification device 147. Similar to the electrical interface 28, the electrical interface 149 may be a direct or non-contact electrical interface. It is also contemplated that the cartridge identification device 147 may be in wireless communication with the controller 22, the adapter identification device 32, or the loading unit identification device 42.

The multi-fire fastener cartridge 143 may include a plurality of sensors 148 (one shown) disposed thereabout to detect various conditions of the multi-fire fastener cartridge 143 or of the environment (e.g., if the multi-fire fastener cartridge 143 is connected to a loading unit, the number of firings available for the multi-fire fastener cartridge 143, the work done by the multi-fire fastener cartridge 143, the temperature within the multi-fire fastener cartridge 143, a peak force during firing of the multi-fire fastener cartridge 143, a total amount of force applied to the multi-fire fastener cartridge 143, a peak retraction force of the multi-fire fastener cartridge 143, a number of pauses during firing of the multi-fire fastener cartridge 143, a thickness of tissue during firing of the multi-fire fastener cartridge 143, etc.). The plurality of sensors 148 provides input to the cartridge identification device 42 in the form of data signals. The data signals of the plurality of sensors 148 may be stored within, or be used to update the cartridge data stored within, the cartridge identification device 147. The data signals of the plurality of sensors 148 may be analog or digital.

The handle 20 includes a transmitter 24 that is configured to transmit instrument data from the controller 22 to other components of the system 100 (e.g., the LAN 104, the cloud 110, the console 120, or the portable device 130). The transmitter 24 may also receive data (e.g., cartridge data, loading unit data, or adapter data) from the other components of the system 100. For example, the controller 22 may transmit instrument data including a serial number of an attached adapter (e.g., adapter 30) attached to the handle 20, a serial number of a loading unit (e.g., loading unit 40) attached to the adapter, and a serial number of a multi-fire fastener cartridge (e.g., multi-fire fastener cartridge 143), loaded into the loading unit, to the console 22. Thereafter, the console 120 may transmit data (e.g., cartridge data, loading unit data, or adapter data) associated with the attached cartridge, loading unit, and adapter, respectively, back to the controller 22.

Figure 3:
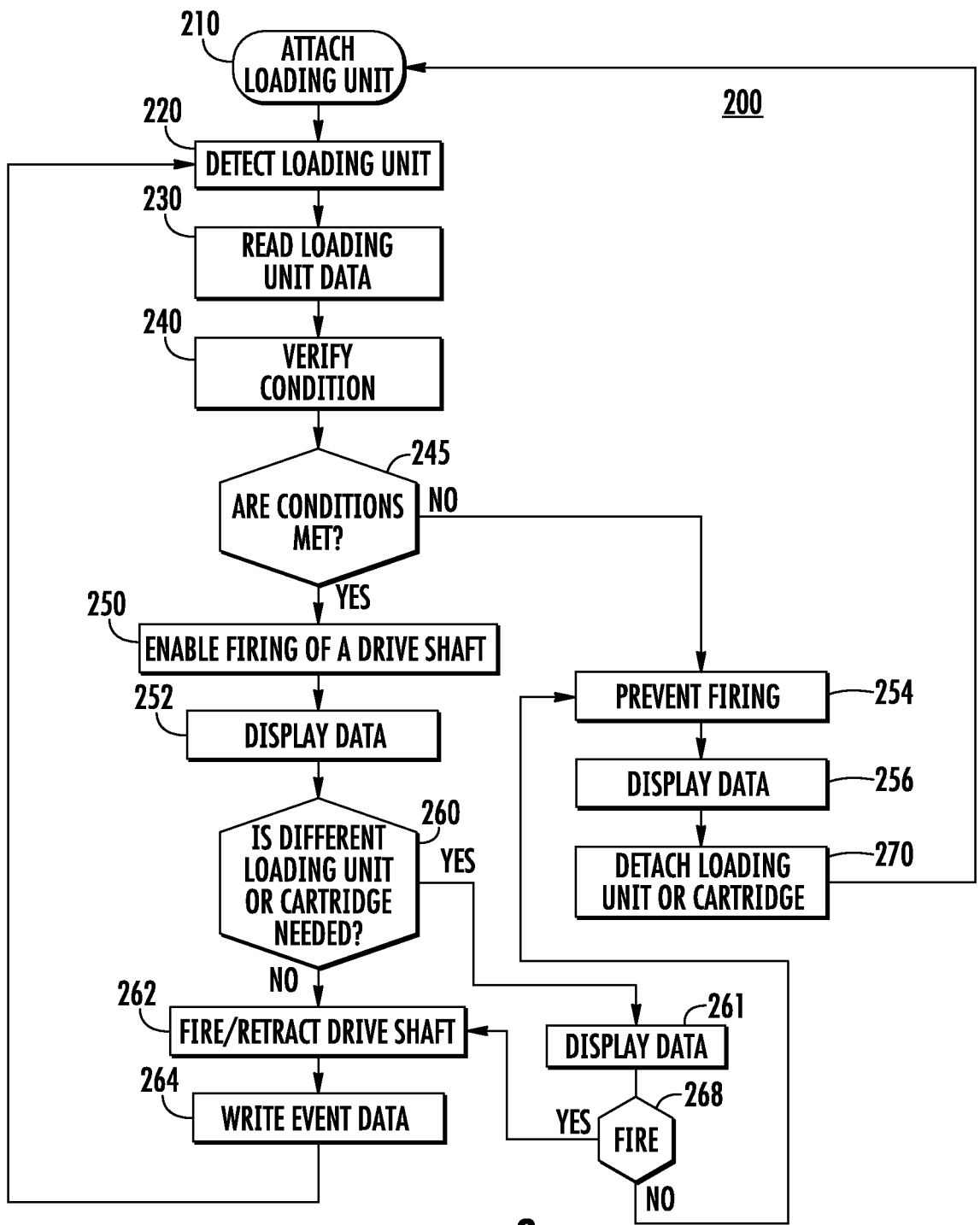
FIG. 3 is a flowchart of an exemplary method of operating the surgical instrument of FIGS. 1 and 2 in accordance with the present disclosure.

Referring to FIGS. 1-3, a method 200 for firing the surgical instrument 10 in accordance with the present disclosure is detailed below. To begin the surgical instrument 10 is assembled by attaching or coupling the adapter 30 to the handle 20 and the loading unit 40 to the adapter 30. In embodiments, a multi-fire fastener cartridge 143 is attached to the end effector 140 of the loading unit 40. It is contemplated that the surgical instrument 10 may be supplied as an assembled surgical instrument 10.

The handle 20 of the surgical instrument 10 is activated or powered "on" when the loading unit 40 is attached to the handle 20 via the adapter 30 (Step 210). When the handle 20 is activated, the controller 22 detects the attached loading unit (e.g., loading unit 40) by receiving data from any attached components (e.g., an adapter or loading unit) (Step 220). If no components (e.g., adapter or loading unit) are attached to the handle 20, the controller 22 may display an error message (e.g., "ATTACH ADAPTER OR LOADING UNIT") on the display 25 or transmit the error message, via transmitter 24, to the console 120 or the portable device 130 to display the error message on the monitor 125 or portable device screen, respectively.

When the adapter 30 is attached to the handle 20 with the loading unit 40 attached to the adapter 30 (Step 210), the controller 22 receives or reads loading unit data and adapter data from the loading unit 40 and the adapter 30 (Step 230), respectively. The controller 22 verifies that the loading unit data and the adapter data meet a plurality of conditions including, but not limited to, whether the adapter 30 and the loading unit 40 are properly attached, that the adapter 30 and the loading unit 40 are compatible with one another and the handle 20, that the loading unit 40 has available actuations, that the previous actuation of the loading unit 40 was completed, that the maximum actuation force required to fire the loading unit 40 is within a predefined range of maximum actuation forces for the adapter 30 and the handle 20, and that the total actuation force or work is within a predefined range of total actuation force or work for the adapter 30 and the handle 20 (Step 240).

If each of the plurality of conditions are met, the controller 22 enables actuation of the drive shaft 23a to permit clamping of the end effector 140 of the loading unit 40 (Step 250). The controller 22 may also display a portion of the loading unit data (e.g., number of actuations available) on the display 25, or transmit the portion of the loading unit data to the console 120 or the portable device 130, or display the portion of the loading unit data on the monitor 125 or portable device screen, respectively (Step 252). It is also contemplated, that the control interface 21 may provide indicia to a user that actuation of the drive shaft 23a is enabled (e.g., a button may light up).

When the actuation of the drive shaft 23a is enabled, a clinician engages the control interface 21 to clamp the jaws 142, 144 of the end effector 140 on tissue to be affected with the instrument 10 (e.g., tissue to be stapled and severed). The plurality of sensors 44, 148 of the loading unit 40 or the multi-fire fastener cartridge 143, respectively, detect tissue properties of the tissue clamped within the end effector 140 and compare the tissue properties (e.g., tissue thickness, tissue type, tissue density, tissue vascularity) to predefined ranges of suitable tissue properties of the loading unit data or the cartridge data (Step 260).

If the tissue properties are within the predefined ranges of suitable tissue properties of the loading unit data or the cartridge data, the controller 22 enables additional actuation of the drive shaft 23a to fire the loading unit 40 (Step 262). The controller 22 may provide indicia to a clinician that actuation is enabled (e.g., a button of the control interface 21 may light up). In some embodiments, when a clinician engages the control interface 21 to clamp tissue within the end effector 140, the controller 22 verifies that the tissue properties are within the predefined ranges of suitable tissue properties and fires the loading unit 40 (e.g., actuates the drive shaft 23a to fire and form staples from the loading unit 40 through the tissue clamped within the end effector 140) without additional input from the clinician. After firing the loading unit 40, the controller 22 reverses the rotation of the drive shaft 23a after ejecting a first set of fasteners from the multi-fire fastener cartridge 143 to permit additional firing of multi-fire fastener cartridge 143, while the loading unit 40 is within the target surgical site. Following a firing, the drive shaft 23a may be rotated such that the jaws 142, 144 are opened.

After firing the loading unit 40, the plurality of sensors 34, 44, 148 of the adapter 30, the loading unit 40, and the multi-fire fastener cartridge 143 collect and transmit data from the firing event to the adapter identification device 32, to the loading unit identification device 42, and to the cartridge identification device 147, respectively. The adapter identification device 32, the loading unit identification device 42, and the cartridge identification device 147 update the adapter, loading unit, and cartridge data, respectively, with the firing event data (Step 264). The controller 22 may calculate a highest peak force applied to the loading unit 40 during the firing of the loading unit and update the adapter, loading unit, and cartridge data, respectively, after the firing of the loading unit 40.

After each firing event, the firing event data may be transmitted to the LAN 104, the cloud 110, the console 120, or the portable device 130 to update the adapter, loading unit, and cartridge data that is stored remote to the surgical instrument 10. The remote storage of the adapter, loading unit, and cartridge data may provide a central repository for data from every surgical instrument (e.g., surgical instrument 10) within a medical facility. In this manner, when an adapter 30 or loading unit 40 is attached to a handle 20, the handle 20 may retrieve previous firing event data of the adapter (e.g., when the loading unit 40 was fired with other handles) or of the loading unit, to receive conditions of the adapter or loading unit not stored within the respective adapter identification device or loading unit identification device. In addition, storing adapter, loading unit, and cartridge data remote to the surgical instrument 10 may provide a redundant source of data if data on the respective component (e.g., adapter 30 or loading unit 40) becomes corrupted. Moreover, the firing event data may be transmitted by or retrieved from the cloud 110 by the manufacturer of the surgical instrument 10 to determine conditions during the use of surgical instrument 10 to improve or develop future product offerings.

The controller 22 then receives or reads loading unit data and adapter data from the loading unit 40 and the adapter 30 (Step 230), respectively, to determine if the plurality of conditions are met for a subsequent firing (Step 262) and/or clamping of tissue (Step 245).

If the plurality of conditions is not met, the controller 22 display an error message (e.g., "INCORRECT STAPLE SIZE," "THICK TISSUE") on the display 25 or transmit the error message, via transmitter 24, to the console 120 or the portable device 130 to display the error message on the monitor 125 or portable device screen, respectively, (Step 261). The clinician may select to fire the loading unit 40 (Step 262) or may select to prevent firing of the cartridge (Step 254). If the clinician selects to prevent firing the controller 22 locks the drive shaft 23a to prevent the loading unit 40 from firing (Step 254). The controller 22 may physically lock or electrically lock (e.g., no power to the motor). The controller 22 may display an error message (e.g., "NO FIRINGS AVAILABLE," "REPLACE LOADING UNIT") on the display 25 or transmit the error message, via transmitter 24, to the console 120 or the portable device 130 to display the error message on the monitor 125 or portable device screen, respectively, (Step 256).

The loading unit 40 or the multi-fire fastener cartridge 143 is then detached from the adapter 30 or the loading unit 40 (Step 270), respectively, and is replaced with a different loading unit 40 or multi-fire fastener cartridge 143 (Step 220). The controller 22 then rereads the loading unit data and the adapter data (Step 230) before verifying the plurality of conditions (Step 240).

Returning to when tissue is clamped within the end effector 140, if the tissue properties are not within the predefined ranges of suitable tissue properties of the loading unit data or the cartridge data, the controller 22 prevents additional actuation of the drive shaft 23a to disable firing of the loading unit 40 (Step 254). The controller 22 may then display an error message on the display 25 or transmit the error message, via transmitter 24, to the console 120 or to the portable device 130, to display the error message on the monitor 125 or portable device screen, respectively, (Step 256). Additionally or alternatively, the controller 22 may provide and display a recommendation message (e.g., "REPLACE WITH 2.5 MM STAPLE CARTRIDGE") on the display 25 or transmit the recommendation message, via transmitter 24, to the console 120 or to the portable device 130, to display the recommendation message on the monitor 125 or on portable device screen, respectively, (Step 256). As detailed above, the loading unit 40 or the multi-fire fastener cartridge 143 is detached (Step 270) and a different loading unit 40 or multi-fire fastener cartridge is attached to the handle 20 and detected by the handle 20 (Step 220). Alternatively, the multi-fire fastener cartridge 143 may be re-fired as needed or desired.

The wireless transmission detailed herein may be radio frequency, optical, WIFI, Bluetooth® (an open wireless protocol for exchanging data over short distances (using short length radio waves) from fixed and mobile devices, ZigBee® (a specification for a suite of high level communication protocols using small, low-power digital radios based on the IEEE 802.15.4-2003 standard for wireless personal area networks (WPANs)), etc.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of actuating a surgical instrument, the method comprising:
   coupling an adapter to a handle, the handle including a controller;
   coupling a loading unit to the adapter, the loading unit including a loading unit identification device;
   reading loading unit data from the loading unit identification device with the controller;
   enabling actuation of the loading unit in response to the loading unit data meeting at least one predefined condition;
   recording event data during actuation of the loading unit; and
   updating the loading unit data with the event data.

2. The method of claim 1, further comprising displaying a portion of the loading unit data on a display of the handle.

3. The method of claim 2, further comprising displaying on the display of the handle a recommended multi-fire fastener cartridge for the loading unit in response to the event data.

4. The method of claim 1, further comprising the controller preventing the loading unit from firing when the loading unit does not meet the predefined conditions.

5. The method of claim 1, further comprising recommending a second loading unit from the loading unit data before enabling actuation of the loading unit.

6. The method of claim 1, further comprising:
   detaching the loading unit from the adapter;
   attaching a second loading unit to the adapter, the second loading unit including a second loading unit identification device;
   reading second loading unit data from the second loading unit identification device with the controller;
   enabling actuation of the second loading unit in response to the second loading unit data meeting the at least one predefined condition;
   recording second event data during actuation of the second loading unit; and
   updating the second loading unit data with the second event data.

7. The method of claim 1, further comprising recommending a second multi-fire fastener cartridge for the loading unit from the loading unit data before enabling actuation of the loading unit.

8. The method of claim 1, further comprising:
   removing a first multi-fire fastener cartridge from the loading unit;
   attaching a second multi-fire fastener cartridge to the loading unit; and
   reading multi-fire fastener cartridge data from a multi-fire fastener cartridge identification device of the second multi-fire fastener cartridge with the loading unit identification device.

9. The method of claim 8, further comprising:
   updating the loading unit data with the loading unit identification device after reading the multi-fire fastener cartridge data of the second multi-fire fastener cartridge; and
   the loading unit data includes at least one of a type of fastener within the second multi-fire fastener cartridge, a production lot number of the second multi-fire fastener cartridge, a serial number of the second multi-fire fastener cartridge, a fastener size of fasters within the second multi-fire fastener cartridge, a completed firing condition of the second multi-fire fastener cartridge, or a manufacturer of the second multi-fire fastener cartridge.

* * * * *